United States Patent [19]

King et al.

[11] Patent Number: 4,853,394

[45] Date of Patent: Aug. 1, 1989

[54] N-('-B-HYDROXYETHYLPIPERID-4-YL ESTERS AND AMIDES

[75] Inventors: Francis D. King; Roger T. Martin; Eric A. Watts, all of Harlow, England

[73] Assignee: Beecham Group p.l.c., Brentford, England

[21] Appl. No.: 926,427

[22] Filed: Nov. 3, 1986

[30] Foreign Application Priority Data

Nov. 2, 1985 [GB] United Kingdom ............... 8527052

[51] Int. Cl.$^4$ ................. C07D 211/58; A61K 31/445
[52] U.S. Cl. .................... 514/329; 544/224; 544/112; 544/124
[58] Field of Search ............... 546/224; 514/329

[56] References Cited

FOREIGN PATENT DOCUMENTS

| 194076 | 1/1955 | Austria | 546/127 |
| 0158265 | 10/1985 | European Pat. Off. | 546/124 |
| 1425706 | 2/1976 | United Kingdom | 546/224 |
| 1586468 | 3/1981 | United Kingdom | 546/224 |
| WO84/03281 | 8/1984 | World Int. Prop. O. | 546/126 |

Primary Examiner—Alan L. Rotman
Attorney, Agent, or Firm—James F. Haley, Jr.; David K. Barr

[57] ABSTRACT

Compounds of formula (I) and pharmaceutically acceptable salts thereof:

Ar—CO—X—Y—Z—OR$_1$  (I)

wherein: Ar is a group of formula (a):

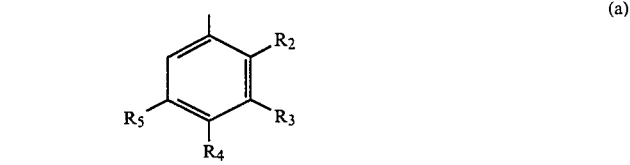

wherein either $R_2$ is $C_{1-6}$ alkoxy and one of $R_3$, $R_4$ and $R_5$ is hydrogen and the other two are selected from hydrogen, halogen, $CF_3$, $CX_{1-6}$ alkylthio, $C_{1-7}$ acyl, $C_{1-6}$ alkoxy, $C_{1-10}$ carboxylic acylamino, $C_{1-6}$ alkyl $S(O)n$ wherein n is 1 or 2, nitro or amino, aminocarbonyl or aminosulphonyl optionally substituted by one or two groups selected from $C_{1-6}$ alkyl, $C_{3-8}$ cycloalkyl, $C_{3-8}$ cycloalkyl $C_{1-4}$ alkyl or phenyl $C_{1-4}$ alkyl groups any of which phenyl moieties may be substituted by one or two groups selected from halogen, $CF_3$, $C_{1-6}$ alkyl or $C_{1-6}$ alkoxy; or $R_2$ is hydrogen and $R_3$, $R_4$ and $R_5$ are independently selected from hydrogen, $C_{1-6}$ alkyl, hydroxy, $C_{1-6}$ alkoxy, $C_{1-6}$ alkylthio or halo; or any two on adjacent carbon atoms together are $C_{1-2}$ alkylenedioxy and the third is hydrogen, $C_{1-6}$ alkyl, $C_{1-6}$ alkoxy or halo;

X is NH; when Ar is of formula (a) and $R_2$ is hydrogen,

Y is a group of formula (c),

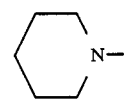

Z is $C_2$ or $C_3$ polymethylene optionally substituted by one or two $C_{1-4}$ alkyl groups; and $R_1$ is hydrogen or $C_{1-6}$ alkyl or $OR_1$ is an in vivo hydrolysable acyloxy group; having gastric motility enhancing activity, anti-emetic activity and/or 5-HT receptor antagonist activity, and their use as pharmaceuticals.

10 Claims, No Drawings

N-('-B-HYDROXYETHYLPIPERID-4-YL ESTERS AND AMIDES

This invention relates to substituted benzamides and benzoates having pharmacological activity, to a process for their preparation and to their use as pharmaceuticals.

J. Pharm and Pharmac. 1977, 29, 147, EP-A-No. 13138, UK Nos. 2100259A and 2125398A, and EP-A-No. 115983 describe aryl amides and esters having a cyclic/bicyclic side chain and possessing pharmacological activity.

A structurally distinct group of compounds has now been discovered which compounds have gastric motility enhancing and/or anti-emetic activity and/or 5-HT receptor antagonist activity.

Accordingly, the present invention provides a compound of formula (I) or a pharmaceutically acceptable salt thereof:

$$Ar-CO-X-Y-Z-OR_1 \quad (I)$$

wherein:
Ar is a group of formula (a):

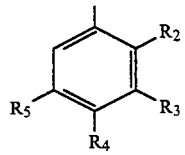

(a)

wherein either $R_2$ is $C_{1-6}$ alkoxy and one of $R_3$, $R_4$ and $R_5$ is hydrogen and the other two are selected from hydrogen, halogen, $CF_3$, $C_{1-6}$ alkylthio, $C_{1-7}$ acryl, $C_{1-6}$ alkoxy, $C_{1-10}$ carboxylic acylamino, $C_{1-6}$ alkyl S(O)n wherein n is 1 or 2, nitro or amino, aminocarbonyl or aminosulphonyl optionally substituted by one or two groups selected from $C_{1-6}$ alkyl, $C_{3-8}$ cycloalkyl, $C_{3-8}$ cycloalkyl $C_{1-4}$ alkyl or phenyl $C_{1-4}$ alkyl groups any of which phenyl moieties may be substituted by one or two groups selected from halogen, $CF_3$, $C_{1-6}$ alkyl or $C_{1-6}$ alkoxy; or $R_2$ is hydrogen and $R_3$, $R_4$ and $R_5$ are independently selected from hydrogen, $C_{1-6}$ alkyl, hydroxy, $C_{1-6}$ alkoxy, $C_{1-6}$ alkylthio or halo; or any two on adjacent carbon atoms together are $C_{1-2}$ alkylenedioxy and the third is hydrogen, $C_{1-6}$ alkyl, $C_{1-6}$ alkoxy or halo;
or Ar is a group of formula (b):

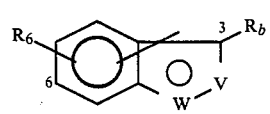

(b)

wherein W is $CH_2$, O, S or $NR_7$ wherein $R_7$ is hydrogen, $C_{1-6}$ alkyl, $C_{3-7}$ alkenyl-methyl, phenyl or phenyl $C_{1-4}$ alkyl either of which phenyl moieties may be substituted by one or two of halogen, $CF_3$, $C_{1-6}$ alkoxy or $C_{1-6}$ alkyl; and V is CH or N; or W is CH or N and V is $NR_a$ where $R_a$ is as defined for $R_7$ above or $CHR_c$ where $R_c$ is as defined for $R_6$ below;

$R_b$ is present when the COX linkage is attached at the phenyl ring, and is selected from hydrogenk, halogen, $CF_3$, hydroxy, $C_{1-6}$ alkoxy or $C_{1-6}$ alkyl;

$R_6$ is hydrogen, halogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulphonylamino, N-($C_{1-6}$ alkylsulphonyl)-N-$C_{1-4}$ alkylamino, $C_{1-6}$ alkylsulphinyl, hydroxy, nitro or amino, aminocarbonyl, aminosulphonyl, aminosulphonylamino or N-(aminosulphonyl)-$C_{1-4}$ alkylamino optionally N-substituted by one or two groups selected from $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups or optionally N-disubstituted by $C_{4-5}$ polymethylene;

X is NH; or O when Ar is of formula (a) and $R_2$ is hydrogen, or when Ar is a group of formula (b);

Y is a group of formula (c), (d) or (e):

(c)

(d)

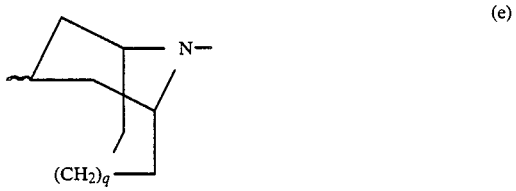

(e)

wherein p and q are independently 0 or 1;
Z is $C_2$ or $C_3$ polymethylene optionally substituted by one or two $C_{1-4}$ alkyl groups; and
$R_1$ is hydrogen or $C_{1-6}$ alkyl or $OR_1$ is an in vivo hydrolysable acyloxy group.

When Ar is a group of formula (a), examples of $R_2$ when $C_{1-6}$ alkoxy include methoxy, ethoxy and n- and iso-propoxy. Preferably $R_2$ is a methoxy group.

Suitable examples of $R_3$, $R_4$ and $R_5$ then include the following atoms and groups: hydrogen; chloro, bromo, $CF_3$, methylthio, ethylthio, n and iso-propylthio; formyl, acetyl, propionyl, n- and iso-butyryl; formylamino, acetylamino, propionylamino, n- and iso-butyrylamino; methyl, ethyl and n- and iso-propylsulphone, -sulphinyl, -thia; nitro; methoxy, ethoxy and n- and iso-propoxy; hydroxy; amino, aminosulphonyl substituted by one or two methyl, ethyl, n- or iso-propyl groups, or by $C_2$, $C_4$ or $C_5$ cycloalkyl or by benzyl optionally substituted as defined above. Particularly suitable $R_4$ and $R_5$ groups include hydrogen, halogen, and amino; and as "intermediates", acylamino and nitro, which can conveniently be converted to the corresponding amino groups.

Particularly preferred $R_4$ groups include 4-amino and 4-acylamino. Most preferably $R_4$ is 4-amino. Particularly preferred $R_5$ groups include 5-halo, such as 5-chloro.

In another group of compounds $R_4$ is hydrogen, 4-halo (eg chloro), or amino; and $R_5$ is 5-$C_{1-6}$ alkyl S (O)$_n$ (such as 5-methylsulphonyl, -sulphinyl or -thia) or 5-optionally alkylated aminosulphonyl.

When $R_2$ is hydrogen, examples of $R_3$ include halo, such as chloro, $C_{1-6}$ alkoxy, such as methoxy, and $C_{1-6}$ alkyl, such as methyl. Preferably $R_3$ is chloro.

Examples of $R_4$ then include hydrogen, halo, such as chloro, hydroxy and $C_{1-6}$ alkoxy such as methoxy. Preferably $R_4$ is hydrogen or chloro.

Examples of $R_5$ then include hydrogen, halo such as chloro, $C_{1-6}$ alkoxy, such as methoxy, and $C_{1-6}$ alkyl, such as methyl. Preferably $R_5$ is hydrogen or chloro. W is often $NR_7$ and V is CH or N; or W is N and V is $NR_a$ wherein $R_a$ is as defined for $R_7$, or W is N and V is $NR_c$ wherein $R_c$ is as defined for $R_6$.

Suitable values for $R_7$ or $R_a$ include hydrogen, methyl, ethyl, n- and iso-propyl; prop-2-enyl, but-2-enyl, but-3-enyl, 1-methylenepropyl, and 1-methylprop-2-yl in their E and Z forms where stereoisomerism exists, phenyl and benzyl optionally substituted by one or two of chloro, bromo, $CF_3$, methoxy, ethoxy, n-and iso-propoxy, methyl, ethyl, n- and iso-propyl. Often $R_7/R_a$ is hydrogen, methyl or ethyl.

Suitable values for $R_b$ when present include hydrogen, chloro, bromo, $CF_3$, methoxy, ethoxy, n- and iso-propoxy, methyl, ethyl, n- and iso-propyl.

Often the -COX- linkage is attached at positions 3 or 6, as depicted in formula (b).

Values for $R_6$ include hydrogen, fluoro, chloro, bromo, $CF_3$, methyl, ethyl, methoxy, ethoxy, methylthio, ethylthio, acetyl, propionyl, acetylamino, methylsulphonylamino, methylsulphinyl, hydroxy, nitro; and amino, aminocarbonyl, aminosulphonyl, aminosulphonylamino or N-(aminosulphonyl)-methylamino any of which may be optionally substituted by one or two methyl groups or by a cyclopentyl or cyclohexyl group or disubstituted by $C_4$ or $C_5$ polymethylene; $R_6$ is often hydrogen or 5-fluoro.

X is often NH.

Examples of Z include $C_2$ or $C_3$ polymethylene optionally substituted by one or two methyl groups.

Z is preferably $-(CH_2)_2-$.

Suitable values for $R_1$ include hydoge, methyl, n- and iso-propyl, n-, iso- and tert-butyl; or $OR_1$ is $C_{1-6}$ alkanoyloxy, propionoxy, benzoyloxy or benzenesulphonyloxy either being optionally substituted in the phenyl ring by one or two substituents selected from $C_{1-4}$ alkyl, $C_{1-4}$ alkoxy, trifluoromethyl, halogen or nitro, or sulphonyloxy groups, for example $C_{1-6}$ alkanesulphonyloxy group, such as methanesulphonyloxy.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascobic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, tartaric, lactic and acetic acid.

Preferably the acid addition salt is the hyrochloride salt.

Examples of pharmaceutically acceptable salts include quaternary derivatives of the compounds of formula (I) such as the compounds quaternised by compounds $R_8$-T wherein $R_8$ is $C_{1-6}$ alkyl, phenyl-$C_{1-6}$ alkyl or $C_{5-7}$ cycloalkyl, and T is a moiety corresponding to an anion of an acid. Suitable examples of $R_8$ include methyl, ethyl and n- and iso-propyl; and benzyl and phenethyl. Suitable examples of T include halide such as chloride, bromide and iodide.

Examples of pharmaceutically acceptable salts of the compounds of formula (I) also include internal salts such as pharmaceutically acceptable N-oxides.

The compouns of the formula (I), their pharmaceutically acceptable salts, (including quaternary derivatives and N-oxides) may also form pharmaceutically acceptable solvates, such as hydrates, and these are included whereever a compound of formula (I), or a salt thereof, is herein referred to.

It will of course be realised that some of the compounds of the formula (I) have chiral or prochiral centres and thus are capable of existing in a number of stereoisomeric forms including enantiomers. The invention extends to each of these stereoisomeric forms (including enantiomers), and to mixtures thereof (including racemates). The different stereoisomeric forms may be separated one from the other by the usual methods.

It will also be realised that compounds of the formula (I) wherein $R_7$ is hydrogen can exist as two tautomeric forms i.e. that wherein $R_7$ is hydrogen and V is CH or N and that wherein $R_a$ is hydrogen and W is N. The invention extends to each of these forms and to mixtures thereof. The predominant tautomeric form is usually that wherein $R_7$ is hydrogen.

It will also be realised that the side chain Y—Z—$OR_1$ may be in an endo or exo orientation with respect to ArCOX. The endo orientation is preferred.

A group of compounds within formula (I) is of formula (II):

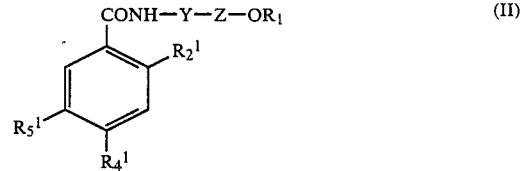

(II)

wherein
$R_2^1$ is $C_{1-6}$ alkoxy;
$R_4^1$ is amino or $C_{1-7}$ alkanoylamino;
$R_5^1$ is halo or $C_{1-6}$ alkylthio;
and the remaining variables are as defined in formula (I). Suitable examples and preferred values for all the variables in formula II are as described for the corresponding variables under formula (I).

There is a further group of compounds within formula (I) of formula (III):

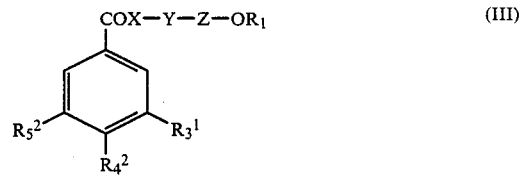

(III)

wherein
$R_3^1$ is halo, $C_{1-6}$ alkoxy or $C_{1-6}$ alkyl;
$R_4^2$ is hydroen or $C_{1-7}$ alkoxy;
$R_5^2$ is halo, $C_{1-6}$ alkoxy or $C_{1-6}$ alkyl; and the remaining variables are as defined in formula (I).

Suitable examples and preferred values for all the variables in formula III are as described for the corresponding variables under formula (I).

There is another group of compounds within formula (I) of formula (IV):

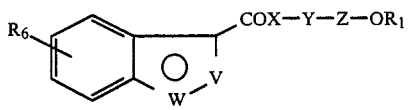
(IV)

wherein the variables are as defined in formula (I).

Suitable examples and preferred values for the variables are as described for the corresponding variables under formula (I).

There are three sub-groups within each of formulae (II) (III) and (IV) wherein $R_1$ is respectively a group of formula (c), (d) or (e) as defined.

The invention also provides a process for the preparation of a compound of formula (I) which process comprises reacting a compound of formula (V):

$$Ar \; G \quad (V)$$

with a compound of formula (VI):

$$L-Y-R_{11} \quad (VI)$$

wherein: G is COQ where Q is a group displaceable by a nucleophile, and L is $NH_2$ or OH or a reactive derivative thereof; $R_{11}$ is $Z-OR_1$ as defined in formula (I) or a hydrogenolysable protecting group; and the remaining variables are as hereinbefore defined; and thereafter optionally converting any $R_1$, $R_3$, $R_4$, $R_5$, $R_6$, $R_a$ and $R_b$ group or $R_{11}$ group to another $R_2$, $R_3$, $R_4$, $R_5$, $R_6$, $R_a$ and $R_b$ group or to $Z-OR_1$ respectively, and optionally forming a pharmaceutically acceptable salt of the resultant compound of formula (I).

Examples of leaving groups Q displaceable by a nucleophile include halogen such as chloro and bromo, hydroxy, carboxylic acyloxy such as $C_{1-4}$ alkanoyloxy or $C_{1-4}$ alkoxycarbonyloxy and activated hydrocarbyloxy such as pentachlorophenoxy.

Alternatively, when G is COQ, Ar is of formula (b) and W is NH in formula (V), a nitrogen heterocycle may act as the leaving group i.e. that obtained by reaction of a compound of formula (V) wherein G is $CO_2H$ with thionyl chloride to give a diindazolo[2,3-a,2',3'-d]-pyrazine-7,14-dione.

If a group Q is a halide, then the reaction is preferably carried out at non-extreme temperatures in an inert non-hydroxylic solvent, such as benzene, dichloromethane, toluene, diethyl ether, tetrahydrofuran (THF) or dimethylformamide (DMF). It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 0°–100° C., in particular 10°–80° C. are suitable.

If a group Q is hydroxy, then the reaction is generally carried out in an inert non-hydroxylic solvent, such as dichloromethane, THF or DMF optionally in the presence of a dehydrating agent such as a carbodiimide, for example dicyclohexylcarbodiimide. The reaction may be carried out at any non-extreme temperature, such as $-10°$ to 100° C., for example, 0° to 80° C. Generally, higher reaction temperatures are employed with less active compounds whereas lower temperatures are employed with the more active compounds.

If a group Q is carboxylic acyloxy, then the reaction is preferably carried out in substantially the same manner as the reaction when Q is halide. Suitable examples of acyloxy leaving groups include $C_{1-4}$ alkanoyloxy and $C_{1-4}$ alkoxycarbonyloxy, in which case the reaction is preferably carried out in an inert solvent, such as dichloromethane, at a non-extreme temperature for example ambient temperatures in the presence of an acid acceptor, such as triethylamine. $C_{1-4}$ alkoxycarbonyloxy leaving groups may be generated in situ by treatment of the corresponding compound wherein Q is hydroxy with a $C_{1-4}$ alkyl chloroformate.

If a group Q is activated hydrocarbyloxy then the reaction is preferably carried out in an inert polar solvent, such as dimethylformamide. It is also preferred that the activated hydrocarbyloxy group is a pentachlorophenyl ester and that the reaction is carried out atambient temperature.

When the leaving group Q is a nitrogen heterocycle as hereinbefore described the reaction is carried out in a similar manner as when Q is a halide.

When L is OH or a reactive derivative thereof, the reactive derivative is often a salt, such as the lithium salt.

Pharmaceutically acceptable salts of the compounds of this invention may be formed conventionally.

The salts may be formed for example by reaction of the base compound of formula (I) with a pharmaceutically acceptable organic or inorganic acid.

It will be apparent that compounds of the formula (I) containing an $R_2$, $R_3$, $R_4$, $R_5$, $R_6$, $R_a$ or $R_b$ group which is convertible to another $R_2$, $R_3$, $R_4$, $R_5$, $R_6$, $R_a$ or $R_b$ group are useful novel intermediates. A number of such conversions is possible not only for the end compounds of formula (I), but also for their intermediates as follows:

(i) a hydrogen substituent is convertible to a nitro substituent by nitration;

(ii) a nitro substituent is convertible to an amino substituent by reduction;

(iii) a $C_{1-7}$ acylamino substituent is convertible to an amino substituent by deacylation;

(iv) an amino substituent is convertible to a $C_{1-4}$ acylamino substituent by acylation with a carboxylic acid derivative;

(v) a hydrogen substituent is convertible to a halogen substituent by halogenation;

(vi) a $C_{1-6}$ alkylthio or $C_{1-6}$ alkylsulphinyl substituent is convertible to a $C_{1-6}$ alkylsulphinyl or a $C_{1-6}$ alkylsulphonyl substituent respectively by oxidation;

(vii) an amino, aminocarbonyl, aminosulphonyl, aminosulphonylamino or N-(aminosulphonyl)-N-$C_{1-4}$ alkylamino substituent is convertible to a corresponding substituent substituted by one or two groups selected from $C_{1-6}$ alkyl, $C_{3-8}$ cycloalkyl, $C_{1-4}$ alkyl or phenyl $C_{1-4}$ alkyl groups any of which phenyl groups may be substituted by one or more groups selected from halogen, trifluoromethyl, $C_{1-6}$ alkyl, $C_{1-6}$ alkoxy and nitro, or disubstituted by $C_{4-5}$ polymethylene, by N-alkylation;

(viii) an amino substituent is convertible to a $C_{1-6}$ alkylsulphonylamino group or an aminosulphonylamino group optionally N-substituted as defined by acylation with a $C_{1-6}$ alkylsulphonyl chloride or di-substituted aminosulphonyl chloride.

(ix) A $C_{1-4}$ alkylamino substituent group is convertible to a N-($C_{1-6}$ alkylsulphonyl)N-$C_{1-4}$ alkylamino group or an N-(aminosulphonyl)N-$C_{1-4}$ alkylamino group optionally N-substituted as defined by acylation with a $C_{1-6}$ alkylsulphonyl chloride or di-substituted aminosulphonyl chloride.

Conversions (i) to (ix) are only exemplary and are not exhaustive of the possibilities.

In regard to (i), nitration is carried out in accordance with known procedures.

In regard to (ii), the reduction is carried out with a reagent suitable for reducing nitroanisole to aminoanisole.

In regard to (iii), deacylation is carried out by treatment with a base, such as an alkali metal hydroxide.

In regard to (iv), (viii), and (ix) the acylation is carried out with an acylating agent, such as the corresponding acid or acid chloride. Formylation is carried out with the free acid.

In regard to (v), halogenation is carried out with conventional halogenating agents.

In regard to (vi), oxidation is carried out at below ambient temperatures in a non-aqueous solvent, such as a chlorinated hydrocarbon, in the presence of an organic peracid, such as 3-chloroperbenzoic acid, or in water in the presence of a soluble strong inorganic oxidant, such as an alkali metal permanganate or in aqueous hydrogen peroxide. It will be realised that this process may also N-oxidise the N-moiety in the side chain and suitable precautions will routinely be taken by the skilled man.

In regard to (vii), alkylation is carried out with a corresponding alkylating agent such as the chloride or bromide under conventional conditions.

Examples of $R_{11}$ when a hydrogenolysable protecting group include optionally substituted benzyl groups, such as benzyl optionally substituted by one or two of halogen, $CF_3$, $C_{1-4}$ alkoxy or $C_{1-4}$ alkyl groups. Such benzyl groups may, for example, be removed, when an Ar substituent(s) is/are other than halogen, by conventional transition metal catalysed hydrogenolysis to give compounds of formula (VIII):

Ar—CO—X—Y—H            (VII)

The invention also provides a further process for the preparation of a compound of formula (I) which comprises N-substituting a compound of formula (VII), and optionally forming a pharmaceutically acceptable salt of the resulting compound of formula (I). In this further process of the invention, 'N-substitution' comprises the substitution of the N-atom in Y in formula (VII) by a group Z—$OR_1$. This may be achieved by reaction of the compound of formula (VII) with a compound $Q_2$—Z—$OR_1$ where $Q_2$ is a leaving group.

Suitable values for $Q_2$ include groups displaced by nucleophiles, such as Cl, Br, I, $OSO_2CH_3$ or $OSO_2C_6H_4CH_3$. Favoured values for $Q_2$ include Cl, Br and I.

The reaction may be carried out under conventional alkylation conditions, for example in an inert solvent such as dimethyformamide, acetone or dimethylsulphoxide in the presence of an acid acceptor such as potassium carbonate. Generally the reaction is carried out at non-extreme temperature such as at ambient or slightly above.

Alternatively, N-substitution may be carried out, when Z is —$(CH_2)_2$— in the resultant compound of formula (I), by reaction with ethylene oxide in an inert solvent such as those described above.

Compounds of formula (I) wherein $R_1$ is H may be converted to compounds wherein $R_1$ is alkyl or $OR_1$ acyloxy by conventional alkylation or acylation methods.

Alkylation is carried out under conventional conditions in an inert solvent at a non-extreme temperature such as ambient temperature or slightly above or at reflux temperature. The alkylating agent has a leaving group that is readily displaceable by a nucleophile. Examples of leaving groups include halide, such as chloride, bromide or iodide, or labile acyloxy groups, such as mesyloxy and tosyloxy.

Acylation is carried out under conventional conditions with an acylating agent which has an acyl group capable of forming an in vivo hydrolysable acyloxy group and leaving group, such as halide, for example chloride and bromide, and hydrogen. When halide is the leaving group, the reaction is generally carried out in the presence of a base. When hydroxy is the leaving group, the reaction is generally carried out in the presence of a dehydrating agent, such as dicyclohexylcarbodiimide, in an inert solvent at non-extreme temperature, such as ambient temperature or slightly above, or reflux temperature.

Compounds of formula (I) wherein $R_1$ is alkyl or $OR_1$ is acyloxy may be converted to compounds wherein $R_1$ is H by dealkylation or hydrolysis respectively.

Dealkylation may be carried out conventionally by warming with aqueous hydrobromic acid or by treatment with pyridine hydrochloride, boron tribromide, boron triiodide or iodotrimethylsilane.

An in vivo hydrolysable acyloxy group is convertible to $R_1$=H by acid or base hydrolysis.

Before carrying out any of these conversions, the effect, if any, on other substituents should be considered, and such reagents as are appropriate should be selected together with the adoption of such precautionary measures as are necessary. For example, O-alkylation and O-acylation may also produce N-alkylated and N-acylated products respectively unless the nitrogen atom(s) is (are) previously protected. This may be achieved by carrying out the alkylation or acylation reaction in a strong acid, such as trifluoroacetic acid, which protonates, and thereby protects, the nitrogen atom(s).

The compounds of formula (V) and (VI) wherein $R_{11}$ is a protecting group are known or are preparable analogously to, or routinely from, known compounds.

Compounds of formula (VI) wherein $R_{11}$ is Z—$OR_1$, other than the compounds wherein Y is of formula (a) and Z is —$(CH_2)_2$— are novel and form an aspect of the present invention.

The compounds of the present invention have gastric motility enhancing and/or anti-emetic activity and/or 5-HT antagonist activity. Compounds having gastric motility enhancing activity are useful in the treatment of disorders such as retarded gastric emptying, dyspepsia, flatulence, oesophageal reflux and peptic ulcer. Compounds having 5-HT antagonist activity are useful in the treatment of migraine, cluster headaches, trigeminal neuralgia and/or cytotoxic agent or radiation induced nausea and vomiting. Examples of cytotoxic agents include cisplatin, doxorubicin and cyclophosphamide. Compounds which are 5-HT antagonists may also be of potential use in the treatment of CNS disorders such as anxiety and psychosis; arrhythmia, obesity and irritable bowel syndrome.

The compounds of formula (I) of interest for their 5-HT antagonist activity are the compounds of formula (I) wherein Ar is of formula (a) and $R_2$ is hydrogen, or Ar is of formula (b). Compounds of formula (I) of particular interest for their gastric motility enhancing activity and anti-emetic activity are the compounds of formula (I) where Ar is of formula (a) and $R_2$ is $C_{1-6}$ alkoxy.

The invention also provides a pharmaceutical composition comprising a compound of formula (I), or a pharmaceutically acceptable salt thereof, and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing.

Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of disorders relating to impaired gastrointestinal motility and/or emesis and/or migraine, cluster headaches, trigeminal neuralgia and/or cytotoxic agent or radation induced vomiting in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.5 to 1000 mg for example 1 to 500 mg, of the compound of the invention. Unit doses may be administered once or more than once a day, for example, 2, 3 or 4 times a day, more usually 1 to 3 times a day, that is in the range of approximately 0.001 to 50 mg/kg/day, more usually 0.002 to 25 mg/kg/day.

No adverse toxicological effects are indicated at any of the aforementioned dosage ranges.

The invention also provides a compound of formula (I) or a pharmaceutically acceptable salt thereof for use as an active therapeutic substance, in particular for use in the treatment of disorders relating to impaired gastrointestinal motility and/or emesis and/or migraine, cluster headaches, trigeminal neuralgia and/or cytotoxic agent or radiation induced vomiting.

The following Examples illustrative the preparation of compounds of formula (I); the following Descriptions illustrate the preparation of intermediates.

DESCRIPTION 1

3α-Amino-8-(β-hydroxyethyl) tropane

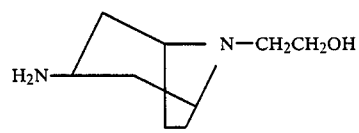

(D1)

Following the procedure described in EP-A-No. 13138, a solution of 8-(β-hydroxyethyl)tropan-3-one oxime (7.0 g) was reduced with sodium (7.0 g) in amyl alcohol (200 ml) to give the crude 3α-amino-8-(β-hydroxyethyl) tropane (ca. 100%).

Prepared similarly was 3α-amino-8-(β-methoxyethyl) tropane.

EXAMPLE 1

4-Acetamido-5-chloro-2-methoxy-N-(1'-β-hydroxyethylpiperid-4-yl)benzamide (E1)

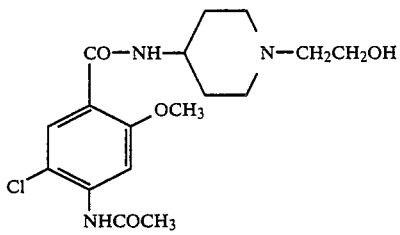

A solution of 4-acetamido-5-chloro-2-methoxybenzoyl chloride (1.0 g), 4-amino-1-β-hydroxyethylpiperidine (E. E. Mikhina and M. V. Rubtsov, Zh. Obshch. Khim., 1963, 33, 2167) (0.54 g) and triethylamine (0.6 ml) in toluene (200 ml) was stirred at r.t. overnight. The product was extracted into 2N HCl (2×20 ml) and re-extracted into $CH_2Cl_2$ (3×50 ml) after basification of the aqueous extract with $K_2CO_3$. The crude product was purified by column chromatography (Alumina, $CHCl_3$) to give E1 (0.4 g, 29%).

| NMR (CDCl$_3$) | | |
|---|---|---|
| δ | 8.18 | (s, 1H) |
| | 8.05 | (s, 1H) |
| | 7.40–8.05 | (m, 2H) |
| | 3.82 | (s, 3H) |
| | 3.20–4.10 | (m, 4H) |
| | 2.18 | (s, 3H) |
| | 0.40–3.20 | (m, 10H) |

EXAMPLE 2

4-Amino-5-chloro-2-methoxy-N-(1'-β-hydroxyethylpiperid-4-yl)benzamide (E2)

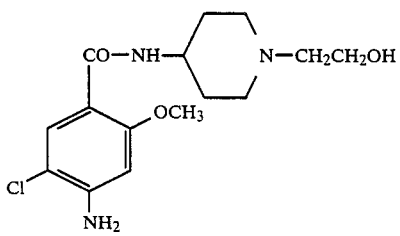

A solution of E1 (0.4 g) in ethanol (10 ml) containing 0.6N NaOH (4 ml) was heated on a steam bath for 1.5 h. The solvent was removed under reduced pressure and the product extracted into $CH_2Cl_2$ (3×40 ml). Recrystallisation of the crude product from ethyl acetate gave E2 (0.23 g, 61%) m.p. 182°–4° C.

| NMR (CDCl$_3$) | | |
|---|---|---|
| δ | 8.09 | (s, 1H) |
| | 7.55–7.73 | (m, 1H) |
| | 6.29 | (s, 1H) |
| | 4.45 | (brs, 2H) |
| | 3.94–4.12 | (m, 1H) |
| | 3.88 | (s, 3H) |
| | 3.56–3.70 | (m, 2H) |
| | 3.03 | (brs, 1H) |
| | 2.76–2.95 | (m, 2H) |
| | 2.50–2.66 | (m, 2H) |
| | 2.22–2.43 | (m, 2H) |
| | 1.95–2.15 | (m, 2H) |
| | 1.46–1.70 | (m, 2H) |

EXAMPLES 3 TO 7

Prepared similarly were:

(exo)-4-Amino-5-chloro-2-methoxy-N—(8'-β-hydroxyethyltropan-3'-yl)benzamide (E3)

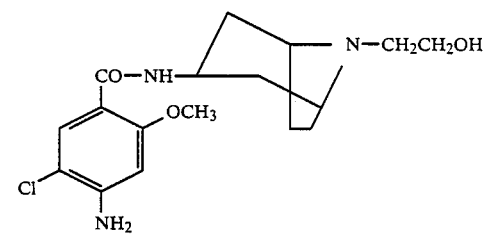

m.p. 219° C.

(exo)-4-Amino-5-chloro-2-methoxy-N—(8'-β-methoxyethyltropan-3'-yl)benzamide (E4)

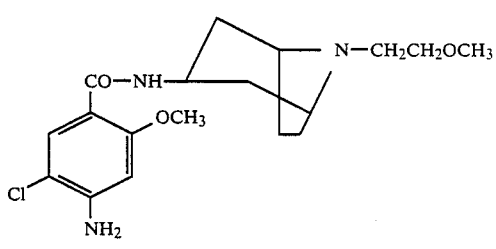

m.p. 168° C.

(endo)-4-Amino-5-chloro-2-methoxy-N—(8'-β-hydroxyethyltropan-3'-yl)benzamide (E5)

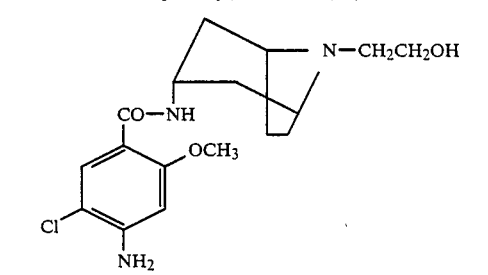

m.p. 189–192° C.

(endo)-4-Amino-5-chloro-2-methoxy-N—(8'-β-methoxyethyltropan-3'-yl)benzamide (E6)

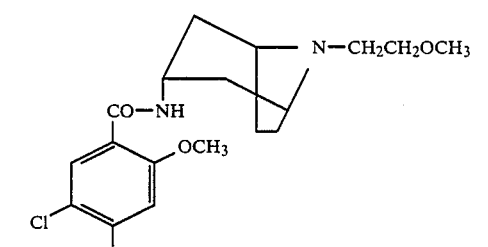

m.p. 190° C.

(endo)-N—(8'-β-hydroxyethyltropan-3'-yl)-1-methylindazole-3-carboxamide (E7)

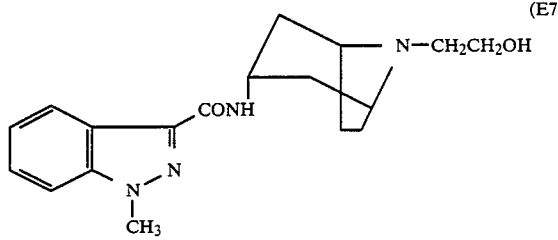

m.p. 263-5° C.

The corresponding 8'β-acetyl derivatives of E5 and E7 are prepared analogously or by acetylation of the corresponding hydroxy compound.

PHARMACOLOGICAL DATA

1. Intragastric Pressure in the Rat

Intragastric pressure changes were recorded from fasted conscious and restrained rats using a saline filled catheter inserted into the lumen of the stomach via a permanent gastric fistula. The catheter was connected to a physiological pressure transducer and pressure changes recorded on a hot wire pen recorder. An index of activity was obtained by measuring the average height of pressure waves during 10 minute periods. Values for 4 such periods were obtained during assessment of spontaneous activity prior to dosing and for the 40 minute period following dosing with compound or vehicle. The Student's "t" test was applied to the mean values obtained for activity prior to and post treatment. Groups of 10 animals were used for each treatment.

The compound of Example 2 had an $ED_{50}$ value of $\leq 0.5$ mg/kg s.c., and the compound of Example 4 had an $ED_{50}$ value of $\leq 1.0$ mg/kg s.c.

2. Intraluminal Pressure in the Heidenhain Pouch of the Dog

Pressure changes were recorded via a saline filled catheter inserted, with airtight closure, into the fistula of a chronic Heidenhain pouch of the previously fasted and lightly restrained conscious dog. The catheter was connected to a physiological pressure transducer and pressure changes recorded on a hot wire pen recorder. Compounds were administered when the motility was in a phase of relatively low activity and the dose range determined which induced an increase in the amplitude of rhythmical contractions for a period of at least 4–5 minutes.

The compound of Examples 2, 5 and 6 were active at a dose of 0.01 mg/kg s.c.

We claim:

1. A compound according formula (II):

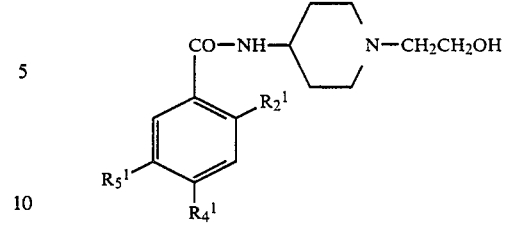

wherein
$R_2^1$ is $C_{1-6}$ alkoxy;
$R_4^1$ is amino or $C_{1-7}$ alkanoylamino;
$R_5^1$ is halo or $C_{1-6}$ alkylthio.

2. A compound according to claim 1 wherein $R_2^1$ is methoxy, $R_4^1$ is amino and $R_5^1$ is chloro, bromo or methylthio.

3. A pharmaceutical composition for the treatment of disorders relating to migraine or cluster headaches comprising an effective amount of a compound of formula (II) as defined in claim 1, or a pharmaceutically acceptable salt thereof, and a pharmaceutically acceptable carrier.

4. A method of treatment of disorders relating to migraine or cluster headaches which comprises the administration of an effective amount of a compound of formula (II) as defined in claim 1, or a pharmaceutically acceptable salt thereof.

5. A pharmaceutical composition for the treatment of disorders relating to trigeminal neuralgia comprising an effective amount of a compound of formula (II) as defined in claim 1, or a pharmaceutically acceptable salt thereof, and a pharmaceutically acceptable carrier.

6. A method of treatment of disorders relating to trigeminal neuralgia which comprises the administration of an effective amount of a compound of formula (II) as defined in claim 1, or a pharmaceutically acceptable salt thereof.

7. A pharmaceutical composition for the treatment of disorders relating to impaired gastro-intestinal motility or emesis comprising an effective amount of a compound of formula (II) as defined in claim 1, or a pharmaceutically acceptable salt thereof, and a pharmaceutically acceptable carrier.

8. A method of treatment of disorders relating to impaired gastro-intestinal motility or emesis which comprises an effective amount of a compound of formula (II) as defined in claim 1, or a pharmaceutically acceptable salt thereof.

9. A pharmaceutical composition for the treatment of disorders relating to impaired gastro-intestinal motility and emesis comprising an effective amount of a compound of formula (I) as defined in claim 1, or a pharmaceutically acceptable salt thereof, and a pharmaceutically acceptable carrier.

10. A method of treatment of disorders relating to impaired gastro-intestinal motility and emesis which comprises the administration of an effective amount of a compound of formula (I) as defined in claim 1, or a pharmaceutically acceptable salt thereof.

* * * * *